United States Patent

Heitmann et al.

[11] Patent Number: 6,123,677
[45] Date of Patent: Sep. 26, 2000

[54] OBTAINING DATA ON HEARING CAPACITY

[75] Inventors: Juergen Heitmann, Wilheim-Schussen-Weg-5; Bernd Waldmann, Gartenstrasse 117, both of D-72074 Tuebingen, Germany

[73] Assignees: Juergen Heitmann; Bernd Waldmann, both of Tuebingen; Peter K. Plinkert, Kusterdingen; Hans-Ulrich Schnitzler; Hans-Peter Zenner, both of Tuebingen, all of Germany

[21] Appl. No.: 09/101,007

[22] PCT Filed: Dec. 11, 1996

[86] PCT No.: PCT/EP96/05527

§ 371 Date: Nov. 9, 1998

§ 102(e) Date: Nov. 9, 1998

[87] PCT Pub. No.: WO97/24065

PCT Pub. Date: Jul. 10, 1997

[30] Foreign Application Priority Data

Dec. 29, 1995 [DE] Germany .................. 195 49 165

[51] Int. Cl.[7] .................................................. A61B 5/00
[52] U.S. Cl. ............................................................. 600/559
[58] Field of Search ........................... 600/559; 128/746; 604/21; 179/11 N

[56] References Cited

U.S. PATENT DOCUMENTS

| | | | |
|---|---|---|---|
| 4,007,731 | 2/1977 | Griffiths et al. | 128/2 Z |
| 4,079,198 | 3/1978 | Bennett | 179/1 N |
| 4,374,526 | 2/1983 | Kemp | 128/746 |
| 4,390,748 | 6/1983 | Zwicker | 179/1 N |
| 5,413,114 | 5/1995 | Zurek et al. | 128/746 |
| 5,601,091 | 2/1997 | Dolphin | 128/746 |

FOREIGN PATENT DOCUMENTS

| | | |
|---|---|---|
| 0 015 258 | 7/1981 | European Pat. Off. . |
| 41 42 257 | 6/1993 | Germany . |

OTHER PUBLICATIONS

Mitteilung aus dem Institut fur Elektroakustic der Technischen Hochschule Munchen, vol. 20, 1968, pp. 206–209 "Der Kubische Differenzton und die Erregung des Gehors", von E. Zwicker.

I INO(1993) 41:339–344, "Der Elinsatz akustischer Distorsionprodukte zur klinischen Diagnostik" by P.K. Plinkeert et al.

J. Acoust. Soc. Am. 77(2), Feb. 1985, "Specification of the acoustical input to the ear at high frequencies" pp. 577–589, S.M. Khanna et al.

IEEE Transactions on Biomedical Engineering, vol. 40, No. 5, May 1993, "Evoked Otoacoustic Emissions, Nonlinearities and Response Interpretation", P. Ravazzani et al.

Hearing Research, Bd. 86, Nr. 1–2, Jun. 1995, DIE Niederlande, Seiten 47–62, Kettembeil et al. "Distortion–product otoacoustic emissions and their anaesthesia sensitivity in the European Starling and the chicken".

*Primary Examiner*—Max Hindenburg
*Assistant Examiner*—Brian Szmal
*Attorney, Agent, or Firm*—Pennie & Edmonds LLP

[57] ABSTRACT

The invention relates to a process for obtaining data on hearing quality by measuring distortion products of otoacoustical emissions (DPOAE) in which two primary tones with the frequencies $f_1$, and $f_2 > f_1$ and sound pressure levels $L_1$ and $L_2$ and at least one sound event having proportions of the frequency $f_3$ and the sound pressure level $L_3$ are applied as stimuli to the hearing organ and at least one distortion product of the defined frequency is determined, where the value of $f_3$ is close to the frequency of the distortion product.

13 Claims, 5 Drawing Sheets

$L_1$ = level of $f_1$
$L_2$ = level of $f_2$
$L_{DP}$ = level of distortion product
$f_{DP}$ = frequency of distortion product
$f_3$ = frequency of suppression tone
x = frequency difference between $f_{DP}$ and $f_3$
$f_1$, $f_2$ = primary tone frequencies D/A = digital/analog converter
A/D = analog/digital converter
LS = loudspeaker
MIC = microphone

OBTAINING DATA ON HEARING CAPACITY

TECHNICAL FIELD

The invention relates to a method for obtaining data on hearing capacity by measuring distortion products of otoacoustic emissions, i.e. by so-called DPOAE measurement.

BACKGROUND OF THE INVENTION

It is popular opinion that the hearing capacity of man representative of vertebrates and, more particularly of mammals, is associated with active amplification processes in the internal ear which, as a whole, improve the sensitivity and frequency resolution of the ear, it being so-called otoacoustical emissions that are viewed as being the epiphenomenon of such processes. These are sound signals emitted by the ear capable of occurring spontaneously or being prompted by external stimulation, i.e. evoked, whereby the stimulation may occur, for example, acoustically or electrically.

The basic significance of evoked otoacoustical emissions for obtaining data as to hearing capacity has been known for a long time. Thus, it is described by Kemp in EP-B1-15258 that sound emissions as a reaction to a sound event can be measured in the outer auditory meatus which relate to the condition in the ear, whereby the otoacoustic emissions were measured by Kemp with the aid of an acoustical probe consisting of a highly-sensitive miniature microphone and a sound transmitter.

It is further known to determine the distortion products of otoacoustical emissions resulting from bitonal stimulation of the hearing organ, the cochlea in man, with two pure tones, so-called primary tones whereby sound emissions occur with the frequencies $nf_1+mf_2$ having the whole numbers n and m. In man it is particularly the so-called cubic distortion product of $2f_1-f_2$ that permits good measurement. However, determining such DPOAE exhibits no good correlation between the amplitude of the distortion product and conventionally measured values for the hearing threshold.

By adding a third stimulus tone as the so-called disturbance tone or suppressor the DPOAE amplitude can be influenced. It is from such measurements that the conclusion arrived at in prior art was that the DPOAE amplitude can be influenced by a suppression tone in the range of the two primary tones, whereas a suppression tone close to the frequency of the distortion product has no influence on the DPOAE amplitude. In this context reference is made to the publication of Plinkert, Harris and Probst in HNO (1993) 41: 339–344 as prior art.

All attempts to date in the field of measuring otoacoustical emissions and distortion products of otoacoustical emissions have in the end the object of providing a method for objectively measuring the hearing capacity. Such a method is thus of great significance because, for example, the (subjective) indications of a human proband as a reaction to the stimulus are no longer required and measurements on all the various hearing organs can be compared to each other.

SUMMARY OF THE INVENTION

The object of the invention is thus to develop such an objective method for measuring the hearing capacity or a method meeting these requirements in the main whilst obviating the cited disadvantages, it also being the intention to develop such a method with an end to providing a corresponding device as well as a probe suitable therefor.

As the stimuli in the method in accordance with the invention two primary tones having the frequencies $f_1$ and $f_2>f_1$ and the sound pressure levels $L_1$ and $L_2$ as well as at least one sound event having components of the frequency $f_3$ and the sound pressure level $L_3$ are applied to the hearing organ and a distortion product of a defined frequency determined, whereby the frequency $f_3$ has a value close to the frequency of the distortion product.

By this method it is achieved, among other things, that the dependency of the emission amplitude of the distortion product on the frequency of the stimuli can be simply determined in comparison. Producing the measurement data of the emission amplitude of the distortion product as a function of the frequency of the stimuli as a so-called DP gram can be sensed with sufficient accuracy with a few measurement points. The disadvantage occurring in routine measurements that the fine structure cannot be sensed with a limitation to a few measurement frequencies is obviated by application of the method in accordance with the invention. As used herein, the expression "close to the frequency of the distortion product" means that the frequency $f_3$ is not located in the range of the frequency $f_2$ or in the range between the frequencies $f_1$ and $f_2$. Preferably frequency $f_3$ is approximated as near as possible to the frequency of the distortion product, whereby this approximation may be restricted by the circumstances of the apparatus employed. For example, for an approximation usable in accordance with the invention the approximation occurs up to frequencies of 10 or 12.5 Hz since thus frequency resolution results from the data transformation system employed. It is usually so that the frequency $f_3$ is not identical to the frequency of the distortion product since it is necessary to split the two frequencies in the measured signal.

In preferred embodiments of the method in accordance with the invention the frequency $f_3$ lies just above the value for the frequency of the distortion product.

As the sound event used as the disturbance tone or suppressor a third (pure) tone having the frequency $f_3$ and the sound pressure level $L_3$ is preferably applied, this then resulting in a stimulation of the hearing organ with three primary tones having the frequencies $f_1$, $f_2$ and $f_3$ and the sound pressure levels $L_1$, $L_2$ and $L_3$.

In a further aspect the sound pressure level $L_3$ of the sound event, especially of the third tone is smaller that the sound pressure level $L_1$ or $L_2$ of at least one primary tone. The basic function requirement is that the sound pressure level $L_3$ for example for a third tone having the frequency $f_3$ must be sufficiently large to achieve the advantages as already, and subsequently to be described. It is usually so that the sound pressure level $L_3$ can be selected smaller, the nearer the frequency $f_3$ is located to the frequency of the distortion product. As mentioned the method can be implemented particularly well when $f_3$ is located slightly above the frequency of the distortion product. The further the frequency $f_3$ is selected away from the frequency of the distortion product the higher the sound pressure level $L_3$ needs to be selected in the normal case.

In further preferred embodiments the sound pressure level $L_3$ of the sound event or of the third tone does not deviate substantially from the sound pressure level $L_2$ of the primary tone with the frequency $f_2$, whereby the sound pressure level $L_3$ can be selected somewhat smaller than the sound pressure level $L_2$. Preferably the sound pressure level $L_3$ equals the sound pressure level $L_2$.

Expedient deviations of the sound pressure level $L_3$ from the sound pressure level $L_2$ lie in the range between −15 dB and +15 dB. Within this range deviations between −10 dB and +10 dB are particularly preferable.

It is basically so that all possible distortion products can be determined in the invention, whereby some distortion products can be determined particularly well, for example due to the intensities of the corresponding sound emissions. In man it is particularly the so-called cubic distortion product $2f_1-f_2$ that can be determined.

Implementing the method in accordance with the invention is done preferably in the so-called audio range, i.e. the "normal" hearing range. Within this range the method is implemented more particularly at frequencies between 500 Hz and 16 kHz, i.e. the frequency of the stimuli is varied within the cited frequency range.

Emitting the stimuli may be done basically during measurement in various ways. Preferably the stimuli, more particularly the primary tones, are applied continuously to the hearing organ. If an intermittent emission of the stimuli to the hearing organ is selected the sound event serving more particularly as the suppressor is employed intermittently.

In the invention the phenomenon resulting from the properties of the measuring apparatus that the analysis time window, i.e. the space in time within which the measurement is made, is limited, can be additionally exploited to advantage. When namely the frequency (in Hertz) of the stimuli is selected as a whole number multiple of the fundamental frequency resulting from the reciprocal of the analysis time window (in seconds) a whole number of waves of all three stimuli materializes for the length of the time window of the subsequent analysis. This necessitates a substantial simplification of the analysis. Accordingly, in the invention preferably a defined coupling of three tones applied to the hearing organ is affected relative to each other, this coupling being prompted in the end by a means for digital data processing involving a digital to-analog conversion in which the timing is correspondingly synchronized by, for example, three digital/analog converters provided to produce three tones.

Furthermore, the method in accordance with the invention may be configured so that in establishing the measurement data, the frequency and sound pressure level of a primary tone, especially $f_2$ and $L_2$ of the second primary tone are defined. Then, on the basis of defined criteria stemming, for example, from tests, advantagous frequency and sound pressure level values for the other primary tone, more particularly the first primary tone with $f_1$ and $L_1$ as well as the suppressor, more particularly the third tone with $f_3f=fDP+X$ are calculated and subsequently the measurement implemented.

In the method in accordance with the invention a calibration may also be provided for so that, for example, the specific circumstances of the auditory meatus of a test person are taken into account individually. For this purpose, prior to commencement of the actual measurement, a stimulus is applied and recorded over all frequencies of interest (white noise). Then in the later measurement for each individual frequency a correction can be made which takes into account the individual configuration of the auditory meatus in each case. When, for example, electroacoustic transducers are used for generating the stimuli then an individual voltage value can be established in the invention for each frequency, this voltage value resulting in the desired sound pressure level at the hearing organ, whereas in prior art it is usually so that constant voltage signals are used irrespective of whether these actually result in the individually desired sound pressure level or not.

Furthermore, an averaging of the measurement data in time for the distortion product determined within time windows can be expediently undertaken in the invention. This is founded in the phenomenon that the actual measurement signal in a single measurement is buried in background noise. This averaging cancels out the noise in a plurality of measurements. In one preferred embodiment of the invention the values obtained during averaging can be calibrated and weighted continually with the ambient or background noise. This achieves that the averaging can be discontinued at any time once a desired signal-to-noise ratio, i.e. a specific spacing between DPOAE signal and the underlying background noise has been achieved with no need for the system to run through a fixed number of cycles (time windows) thus enabling the measurement duration to be shorted as a whole.

The hearing organ as mentioned is preferably a hearing organ of vertebrates, more particularly of mammals. In the case of mammals and man the hearing organ involved may be more particularly the cochlea.

The profile of the plots measured in the invention, in which the fine structure is obliterated in part and so-called "flat" DP grams will now be described with reference to the Figures. One explanation of the advantages of the method in accordance with the invention can be attributed to the fact that the fine structure of a DP gram is to be attributed to the interference of two spatially separated generation mechanisms or generators for the emission at the frequency of the distortion product. It can be assumed that the distortion product in man materializes in the region of the basilar membrane of the cochlea in which the two primary tones overlap, resulting in distortions evident in the form of distortion products due to the non-linear response of the cochlean amplifier in the overlapping range of the frequencies $f_1$ and $f_2$ and thereby in the region of $f_2$. These distortion tones disseminate from their point of origin and thus attain the middle ear and produce via the ear drum a sound pressure which can be measured in the auditory meatus. Furthermore, these distortion tones disseminate also in the opposite direction, resulting in at the location representing $2f_1-f_2$ a deflection of the basilar membrane caused by resonance. This oscillation is amplified by the active cochlearan process and disseminates likewise retrograde to the middle ear by stimulus frequency otoacoustic emission (SFOAE). As a result of this two sinusoidal tones having the same frequency, namely the frequency of the distortion product, appear in the ear drum and in the auditory meatus, which stem, however, from two spatially separated emission locations, namely the cited location in the region of $f_2$ and from the location with $f_{dp}$. These two signals interfere as a function of the relative phase angle, it being this phase angle differing as a function of the frequency that the fine structure with its sequence of minima and maxima (rippling) can be attributed to.

By applying a competing suppressor in accordance with the invention the stimulus frequency otoacoustic emission (SFOAE) at the frequency $f_{dp}$ can now be separately disabled. A suppressor in the vicinity of the frequency of the distortion product draws the energy of the amplifier to its frequency, thus permitting an explanation too, of why the suppression depends on the frequency and sound pressure level of the suppressor as cited.

Accordingly the invention comprises in general a method of obtaining data on the hearing capacity by measuring the distortion products of otoacoustic emissions (DPOAE) in which two primary tones having the frequencies $f_1$ and $f_2>f_1$ and the sound pressure levels L1 and L2 are applied to the hearing organ as stimuli and at least one distortion product having a defined frequency determined, whereby in this method with the presence of at least two generators or generation mechanisms for the distortion product at least one of these generators or generation mechanisms is suppressed. Such a suppression may be done in absolutely any way possible and is basically not restricted to application of sound events. If sound events are used for suppression the method claimed additionally comprises at least one of the features as described above, reference thus being made to the description as hitherto.

The invention comprises furthermore a device for obtaining data on hearing capacity by measuring DPOAE, more particurly for implementing a method as set forth herein. This device comprises first means for generating at least three stimuli, more particularly acoustic stimuli, second means for detecting otoacoustic emissions, more particularly the sound emissions associated therewith, and third means for controlling and analyzing, more particularly for generating stimuli as well as acquiring and decoding the measurement data.

The first means may comprise more particularly so-called electroacoustic transducers as known from prior art, whereby basically an electroacoustic transducer may be provided for generating two or more stimuli. Thus, for example, an electroacoustic transducer may produce a primary tone and the suppression stimulus (suppression tone), it being preferred, however, in accordance with the invention to provide a separate transducer for each stimulus, i.e. three electroacoustic transducers for two primary tones and a suppression tone.

In one aspect the second means comprise at least one microphone for detecting the evoked sound events, whereby several microphones, for instance, four may be provided, from which measurement values are obtained.

The third means comprise preferably a means for digital data processing with the associated digital-to-analog conversion and analog-to-digital conversion, whereby for generating two primary tones and a stimulus, more particularly a suppression tone, three digital/analog converters are provided. Correspondingly, for detecting the evoked sound events an analog/digital converter is provided.

As regards the further configuration of the device in accordance with the invention reference is made to the description of the corresponding passages of the method in accordance with the invention to which explicit reference is made in this respect.

In conclusion the invention comprises a probe or a sensing head for obtaining data on hearing capacity which is assigned at least three means for the emission of sound stimuli, more particularly tones of a defined frequency and at least one means for detecting sound emissions, the means for emitting sound stimuli being preferably electroacoustic transducers and the detection means being preferably a microphone. The probe (sensing head) described is provided more particularly for implementing the method as described or for the device as described.

In another aspect all means, i.e. preferably three electroacoustic transducers and a microphone are integrated in the probe, as a result of which a compact design is achieved with the means arranged as near as possible to the measurement site.

In preferred embodiments the probe can be introduced at least in part into the external auditory meatus of a mammal, more particularly, of a human-being, this likewise enhancing the measuring accuracy. In addition a sealing element may be provided for more or less excluding the influence of disturbing external sound events (ambient sound).

The described features and further features of the invention materialize from the following description of preferred embodiments in conjunction with the sub-claims, the drawings and the example, whereby the individual features may be achieved each alone or as several in combination with each other.

DETAILED DESCRIPTION OF THE INVENTION

Figure 1:
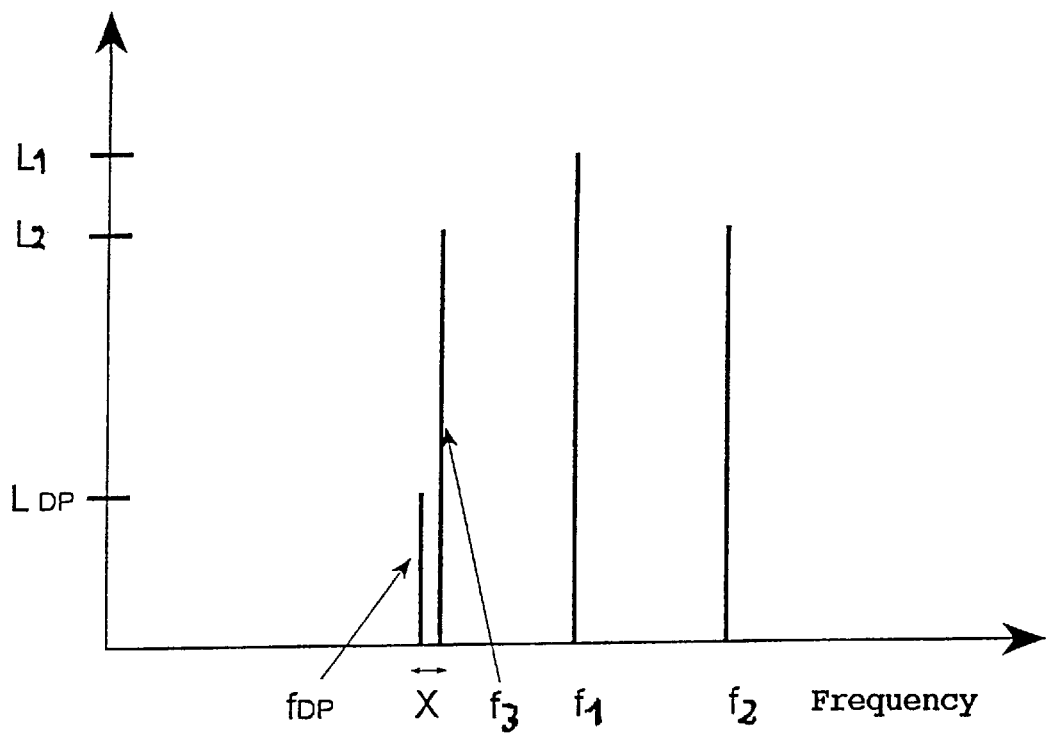
FIG. 1 is a plot of amplitude versus frequency.

FIG. 1 simultaneously depicts the basic principles and substantial features of the invention. The symbols and abbreviations used are explained in the key to the Figure.

The bar lines at the frequencies $f_1$ and $f_2$ symbolize the two primary tones with the sound pressure levels $L_1$ and $L_2$, as illustrated the second primary tone having a higher frequency than that of the first primary tone for a lesser sound pressure level $L_2$. The distortion product having the sound pressure level LDP is symbolized by the bar line at the frequency fDP. Shown just above at higher frequencies is a suppression tone having the frequency $f_3$, the difference between the frequency of the distortion product and the frequency of the suppression tone being x. The sound pressure level $L_3$ of the suppression tone is selected to equal the sound pressure level $L_2$ of the second primary tone.

Figure 2:
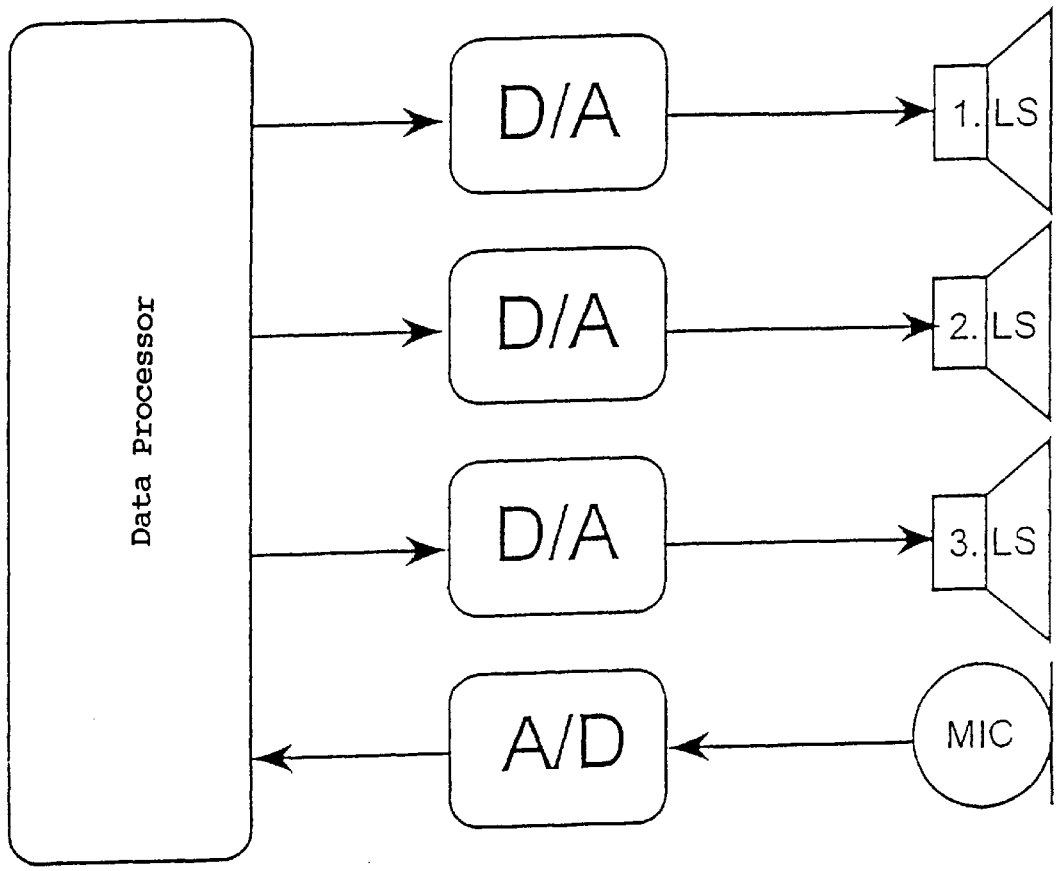
FIG. 2 is a block diagram of one embodiment of the device in accordance with the invention.

The block diagram as shown in FIG. 2 is a schematic illustration of the main components of a device in accordance with the invention, the relative abbreviations and symbols being explained in the key. As evident from FIG. 2 the device comprises three digital/analog converters and an analog/digital converter assigned to an analyzer and control means identified in FIG. 2 quite generally as a data processor. With the aid of this data processor the converters are controlled, i.e. ultimately generating the stimuli applied to the hearing organ and analyzing the evoked sound events. Each of the digital/analog converters is connected to a loudspeaker which produces the actual sound stimulus of the electroacoustic transducers formed as a whole. The analog/digital convertor is connected to a microphone with the aid of which the evoked sound event is detected.

Figure 3:
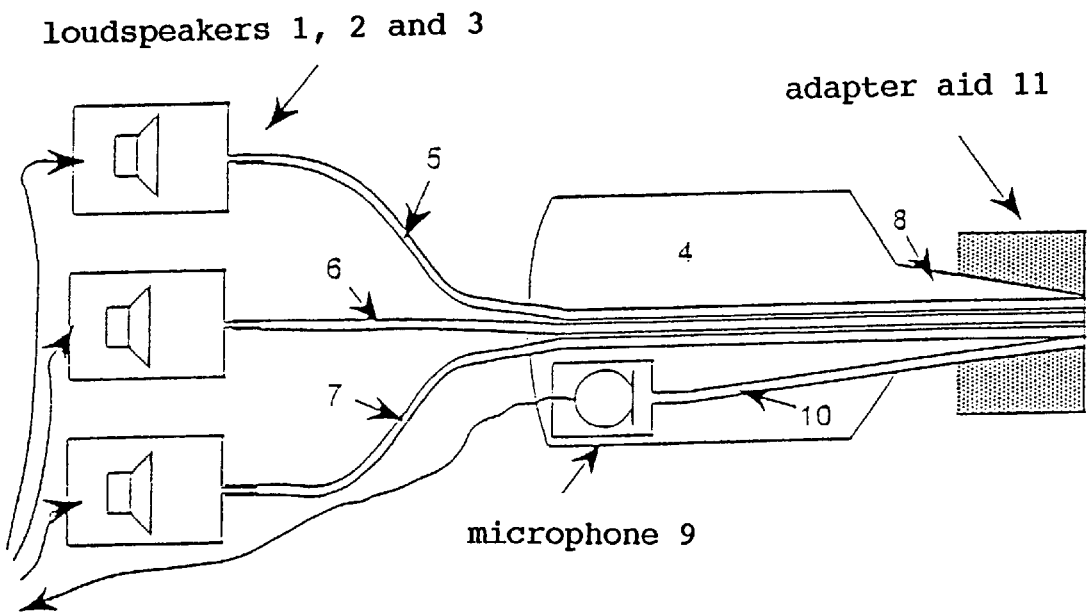
FIG. 3 is a schematic illustration of a probe in accordance with the invention.

FIG. 3 is a schematic view of a probe assigned three loudspeakers 1, 2 and 3 as well as a microphone 9. The three loudspeakers are connected to the actual probe body via tubes 5, 6 and 7 which are guided therethrough to a probe tip 8. In the present case a microphone 9 is integrated in the probe body 4 and likewise guided via a thin tube 10 into the probe tip 8. As already mentioned the loudspeakers 1, 2 and 3 may also be additionally integrated in the probe body 4.

Arranged at the outer circumference of the probe tip 8 pointed, more particularly, conically tapered in the direction of the hearing organ is an adapter aid 11 serving to better introduce and subsequently site the probe in the external auditory meatus. The adapter aid 11 is fabricated preferably of a soft, flexible material.

Figure 4:
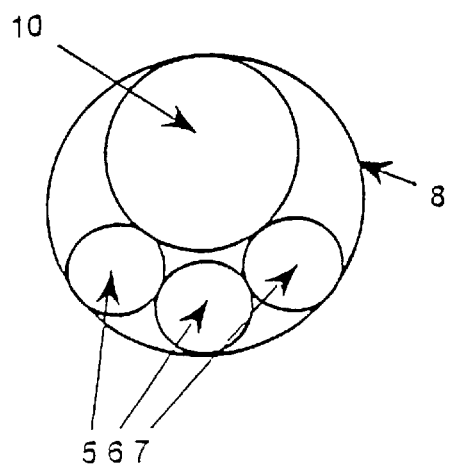
FIG. 4 is a cross-section through the tip of a probe as shown in FIG. 3.

FIG. 4 is cross-sectional view of the probe tip 8, showing each of the ends of the thin tubes 5, 6, 7 and 10. These tubes are open in the direction of the hearing organ so that between the loudspeakers 1, 2 and 3 and the microphone 9 and the ear drum (not shown in the Fig.) an air cushion exists throughout. In accordance with FIG. 4 the tube 10 for the microphone 9 has a larger cross-section than that of the three tubes 5, 6 and 7 of the loudspeakers 1, 2 and 3.

EXAMPLE

DPOAE measurements are implemented in the ear of a test person. In this arrangement the device or probe as illustrated in the FIGS. may be employed with which primary tones having sound pressure levels of $L_1$=65 dB SPL and $L_2$=55 dB SPL are applied at various frequencies with and without use of a suppression tone (suppressor) via external ear and middle ear to the cochlea.

Figure 5:
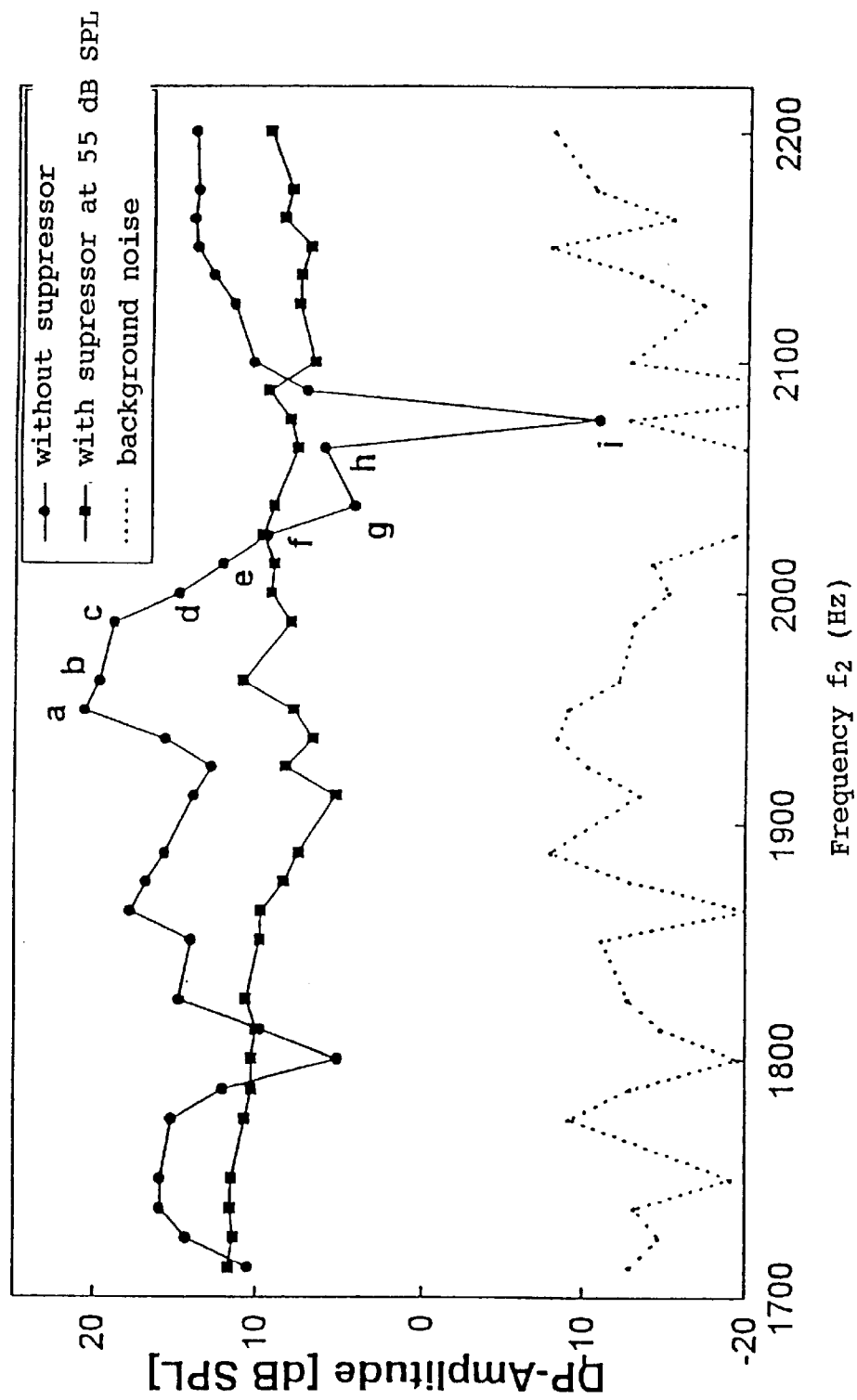
FIG. 5 is a DP gram.
Figure 6:
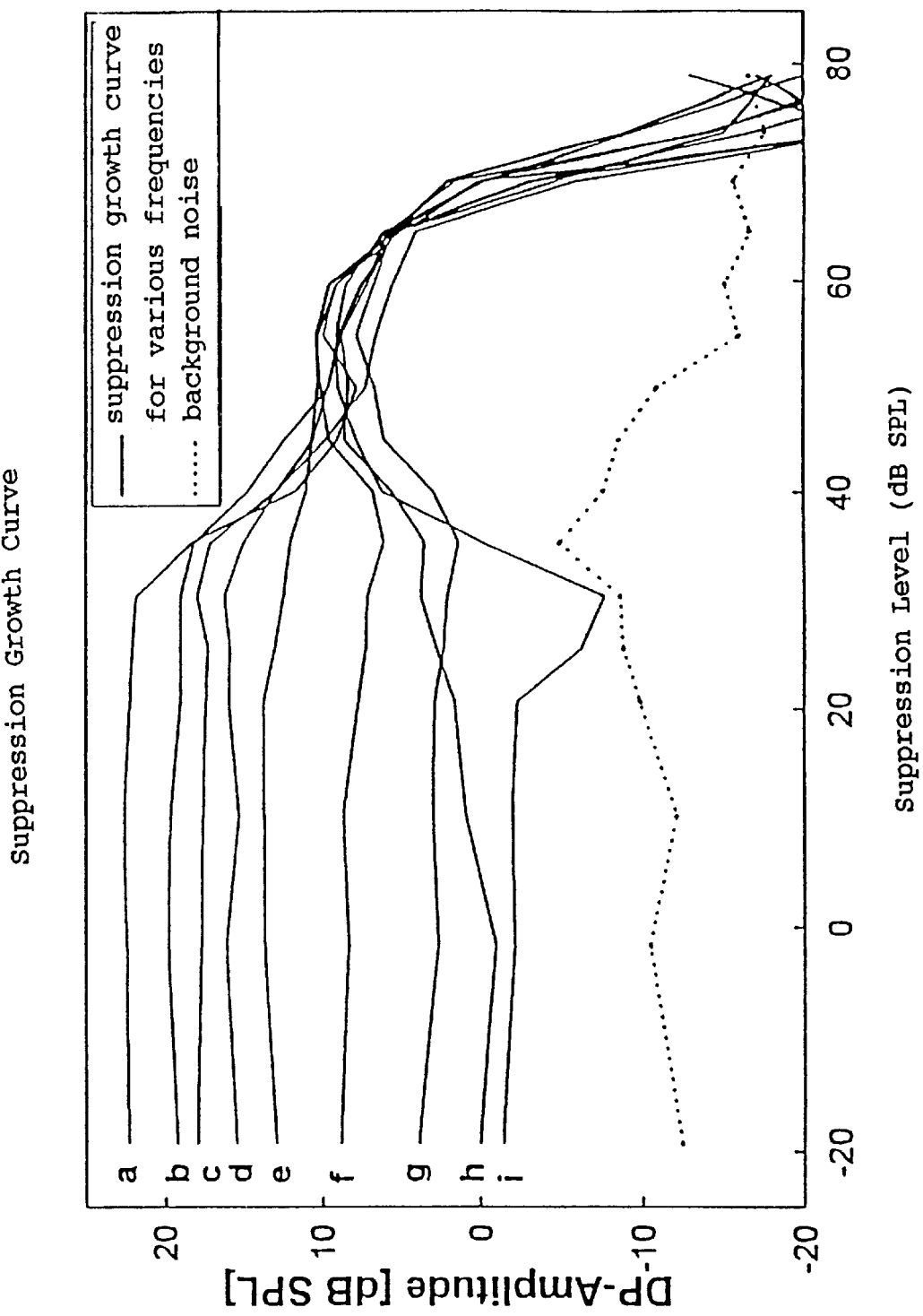
FIG. 6 is a plot of suppression growth curves.

The two FIGS. 5 and 6 serve to explain the measurement results obtained in the example.

FIG. 5 is a plot of the amplitude of the measured distortion product $2f_1-f_2$ as a function of the frequency of the second primary tone, the dots symbolizing the points of measurement without application of a suppression tone whilst the squares symbolize points of measurement in which the hearing organ is irradiated with a suppression tone having the frequency $2f_1-f_2$ +12.5 Hz and a volume of 55 dB SPL.

FIG. 5 shows that the plot with out suppressor, exhibiting high fuzziness in the magnitude of the jumps in amplitude between adjacent minima and maxima which can be translated by the method in accordance with the invention into a relative smooth curve exhibiting hardly any more pronounced jumps in amplitude. Reference is to be made to the theory already discussed in the background description as regards the explanation of this effect.

FIG. 6 shows the suppression effect as a function of the volume of the suppression tone. This suppression response differs considerably depending on the frequency of the stimulus tones. Whereas the distortion product amplitude is reduced in the range of a maximum in the fine structure the emission amplitude is amplified in the regions of a minimum. This phenomenon is evident in both the smoothing effect as shown in FIG. 5 and in the growth curves evident from FIG. 6 in which the measurement points identified a to i in FIG. 5 are plotted as a function of the volume of the suppression tone.

In accordance with the theory as discussed the reduction and increase in the emission amplitude with variation of the suppression level can be explained via the interference between two equal signals the same and opposite in phase.

In implementing the method in accordance with the invention the inhibiting or amplifying effect of a second generator for the distortion product is eliminated and the measured signal is to be attributed exclusively to the other generator and thus this (main) generator, permitting as in the present case conclusions as to the condition of the internal ear, can be reliably determined. The remaining signal is associated only with the condition of the internal ear at the location of the remaining generator, i.e. at the $(2f_1-f_2)$ distortion product with the location at the frequency $f_2$ and is no longer a mixed signal.

Finally, FIG. 6 shows that in the case illustrated at suppression levels as of approx 35 dB SPL a first suppression effect commences, resulting in an amplification of the emission in the curves relative to g, h, i. This suppression effect is evident up to a sound pressure level of the suppression tone of approx. 65 dB SPL. It is not until above this suppression level that the suppression tone influences the other ("main generator") at $f_2$, the determination of which is desired in the absence of disturbing effects. In the range between a suppression level of 45 dB SPL and 65 dB SPL there is practically no change at all in the DP amplitude in the present case, i.e. irrespective of at which frequency the measurement is made. Although this effect as described differs from one person to another in pronouncement it can be demonstrated for any individual.

What is claimed is:

1. A method for obtaining data on hearing capacity by measuring distortion products of otoacoustic emissions in which two primary tones having frequencies $f_1$ and $f_2>f_1$ and the sound pressure levels $L_1$ and $L_2$ as well as at least one sound event having components of a frequency $f_3$ and a sound pressure level $L_3$ are applied to a hearing organ and a distortion product of a defined frequency is determined, whereby the frequency $f_3$ has a value close to the frequency of the distortion product.

2. The method as set forth in claim 1, wherein a third tone having the frequency $f_3$ and the sound pressure level $L_3$ is applied as the sound event.

3. The method as set forth in claim 1, wherein the sound pressure level $L_3$ of the sound event is smaller than the sound pressure level $L_1$ or $L_2$ of at least one primary tone.

4. The method as set forth in claim 1, wherein the sound pressure level $L_3$ of the sound event does not substantially deviate from the sound pressure level $L_2$ of the primary tone having the frequency $f_2$.

5. The method as set forth in claim 4, wherein the sound pressure level $L_3$ of the sound event is equal to or slightly smaller than the sound pressure level $L_2$ of the primary tone having the frequency $f_2$.

6. The method as set forth in claim 1, wherein the sound pressure level $L_3$ of the sound event deviates from the sound pressure level $L_2$ of the primary tone having the frequency $f_2$ by from about −10 dB to about +10 dB.

7. The method as set forth in claim 1, which further includes determining a $(2f_1-f_2)$ distortion product.

8. The method as set forth in claim 1, wherein said method is implemented at frequencies between about 500 Hz and 16 kHz.

9. The method as set forth in claim 1, wherein emission of stimuli to the hearing organ is continuous.

10. The method as set forth in claim 1, wherein emission of stimuli to the hearing organ is intermittent.

11. The method as set forth in claim 1 which further comprises intercoupling three tones applied to the hearing organ by means for digital data processing utilizing digital-to-analog conversion.

12. The method as set forth in claim 1 which further comprises averaging the measured distortion products in time for the distortion product determined within time windows, wherein the values obtained from said averaging are continually weighted in comparison with ambient or background noise.

13. The method as set forth in claim 1, wherein the hearing organ is selected from the group consisting of mammalian cochlea and human cochlea.

* * * * *